(12) United States Patent
Thiagarajan et al.

(10) Patent No.: US 7,806,833 B2
(45) Date of Patent: Oct. 5, 2010

(54) SYSTEMS AND METHODS FOR ANALYSIS AND DISPLAY OF HEART SOUNDS

(75) Inventors: Arvind Thiagarajan, Chennai (IN);
Tat-Jin Teo, Sunnyvale, CA (US);
Damon J. Coffman, Portland, OR (US)

(73) Assignee: HD Medical Group Limited, Victoria (AU)

(*) Notice: Subject to any disclaimer, the term of this patent is extended or adjusted under 35 U.S.C. 154(b) by 642 days.

(21) Appl. No.: 11/740,906

(22) Filed: Apr. 26, 2007

(65) Prior Publication Data
US 2009/0012415 A1    Jan. 8, 2009

Related U.S. Application Data

(60) Provisional application No. 60/833,385, filed on Jul. 25, 2006.

(30) Foreign Application Priority Data
Apr. 27, 2006   (IN) .......................... 772/CHE/2006

(51) Int. Cl.
*A61B 5/02* (2006.01)
(52) U.S. Cl. .......................... 600/528; 600/586; 381/67
(58) Field of Classification Search .......... 600/526–530
See application file for complete search history.

(56) References Cited

U.S. PATENT DOCUMENTS

| 3,799,147 | A | * | 3/1974 | Adolph et al. | ............... | 600/513 |
| 3,878,832 | A | * | 4/1975 | Tickner et al. | ............... | 600/508 |
| 4,182,315 | A | * | 1/1980 | Vas et al. | .................... | 600/500 |

(Continued)

FOREIGN PATENT DOCUMENTS

WO    WO/2005/123180    12/2005

OTHER PUBLICATIONS

Stefadouros, M.D., Miltiadis A. and Calhoun Witham, M.D., "Systolic Time Intervals by Echocardiography," Circulation Journal of the American Heart Association; 1975, vol. 51, pp. 114-117.

(Continued)

*Primary Examiner*—Carl H Layno
*Assistant Examiner*—Paula J Stice
(74) *Attorney, Agent, or Firm*—Kang Lim

(57) ABSTRACT

An auscultation system aids a clinician's diagnosis of the heart sounds by visually displaying at least an S1 heart sound and an S2 heart sound, and ascertaining an onset of at least one of the heart sounds. A corresponding audio representation of the heart sounds can be provided to the clinician. The auscultation system includes a sensor for sensing heart sounds from at least one chest location of the patient and for transducing the heart sounds into electrical signals. The auscultation system also includes a signal processor for selectively filtering the electrical signals thereby highlighting frequency differences of the heart sounds, and further includes a video display for selectively displaying the selectively filtered electrical heart signals. In some embodiments, the auscultation system also displays calipers corresponding to the time domain and the frequency domain of the heart sounds, permitting the clinician to zoom in and out portions of the heart sounds of particular interest and also to take more accurate measurements of these portions of the heart sounds.

21 Claims, 17 Drawing Sheets

U.S. PATENT DOCUMENTS

| | | | |
|---|---|---|---|
| 4,672,977 | A | 6/1987 | Kroll |
| 5,012,815 | A | 5/1991 | Bennett, Jr. et al. |
| 5,213,108 | A | 5/1993 | Bredesen et al. |
| 6,278,890 | B1 | 8/2001 | Chassaing et al. |
| 6,368,283 | B1 * | 4/2002 | Xu et al. .............. 600/485 |
| 6,512,830 | B1 * | 1/2003 | Orten ..................... 381/67 |
| 6,520,924 | B2 * | 2/2003 | Lee ........................ 600/586 |
| 6,910,005 | B2 | 6/2005 | Bartoski |
| 7,174,203 | B2 | 2/2007 | Arand et al. |
| 7,300,407 | B2 | 11/2007 | Watrous |
| 2002/0151812 | A1 * | 10/2002 | Scheiner et al. ............ 600/528 |
| 2003/0045805 | A1 | 3/2003 | Sheldon et al. |
| 2003/0083582 | A1 | 5/2003 | Hirsh |
| 2003/0093002 | A1 * | 5/2003 | Kuo ....................... 600/528 |
| 2003/0163058 | A1 | 8/2003 | Osypka et al. |
| 2004/0028236 | A1 * | 2/2004 | Chelen .................... 381/67 |
| 2004/0106961 | A1 * | 6/2004 | Siejko et al. ............... 607/17 |
| 2004/0260188 | A1 * | 12/2004 | Syed et al. ................ 600/509 |
| 2005/0137490 | A1 * | 6/2005 | Scheiner et al. ............ 600/528 |
| 2006/0173336 | A1 | 8/2006 | Goubergen |
| 2007/0043299 | A1 | 2/2007 | Wariar et al. |
| 2008/0039733 | A1 | 2/2008 | Unver et al. |
| 2008/0154144 | A1 | 6/2008 | Unver et al. |
| 2008/0167566 | A1 | 7/2008 | Unver et al. |

OTHER PUBLICATIONS

"International Search Report and the Written Opinion of the International Searching Authority", Application No. PCT/US06/12611, mailed Sep. 19, 2007.

"International Search Report and the Written Opinion of the International Searching Authority", Application No. PCT/US07/17608, mailed Jan. 28, 2008.

ISA/KR, PCT International Search Report and Written Opinion, Application No. PCT/US2008/086493, dated Apr. 23, 2009, 9 pages.

ISA/US, PCT International Search Report and Written Opinion, Application No. PCT/US2007/010272, dated Oct. 14, 2008, 7 pages.

* cited by examiner

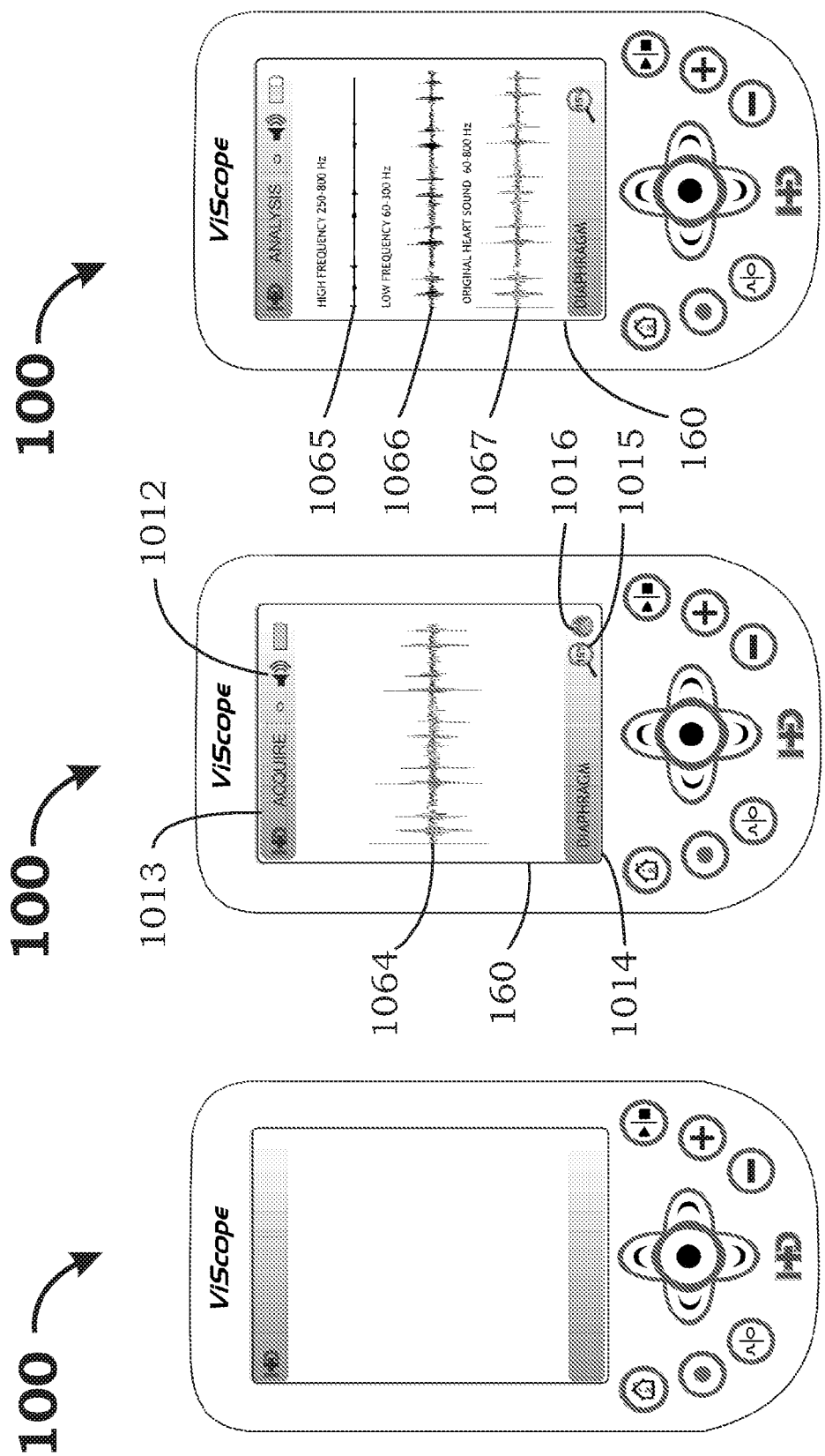

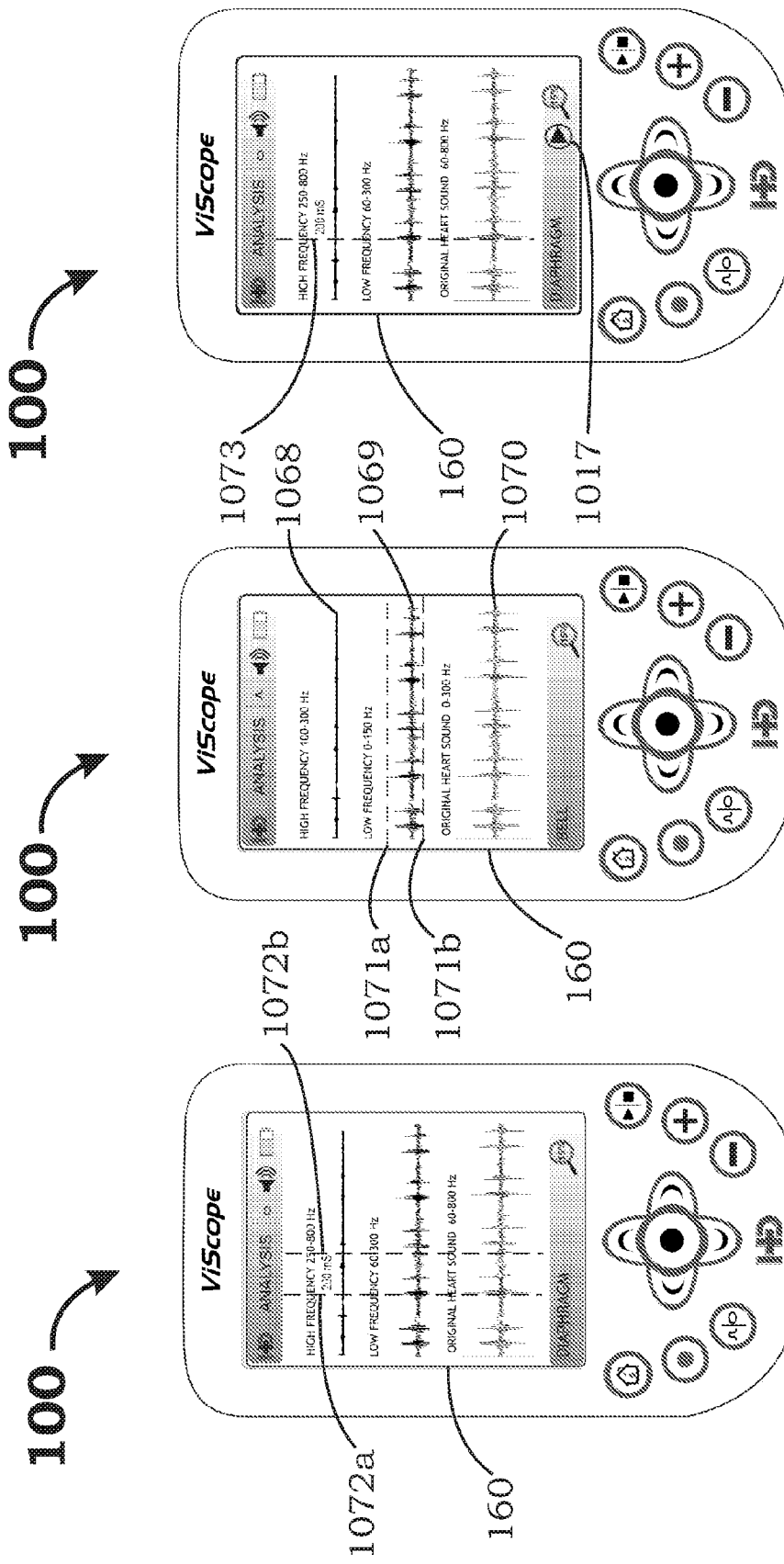

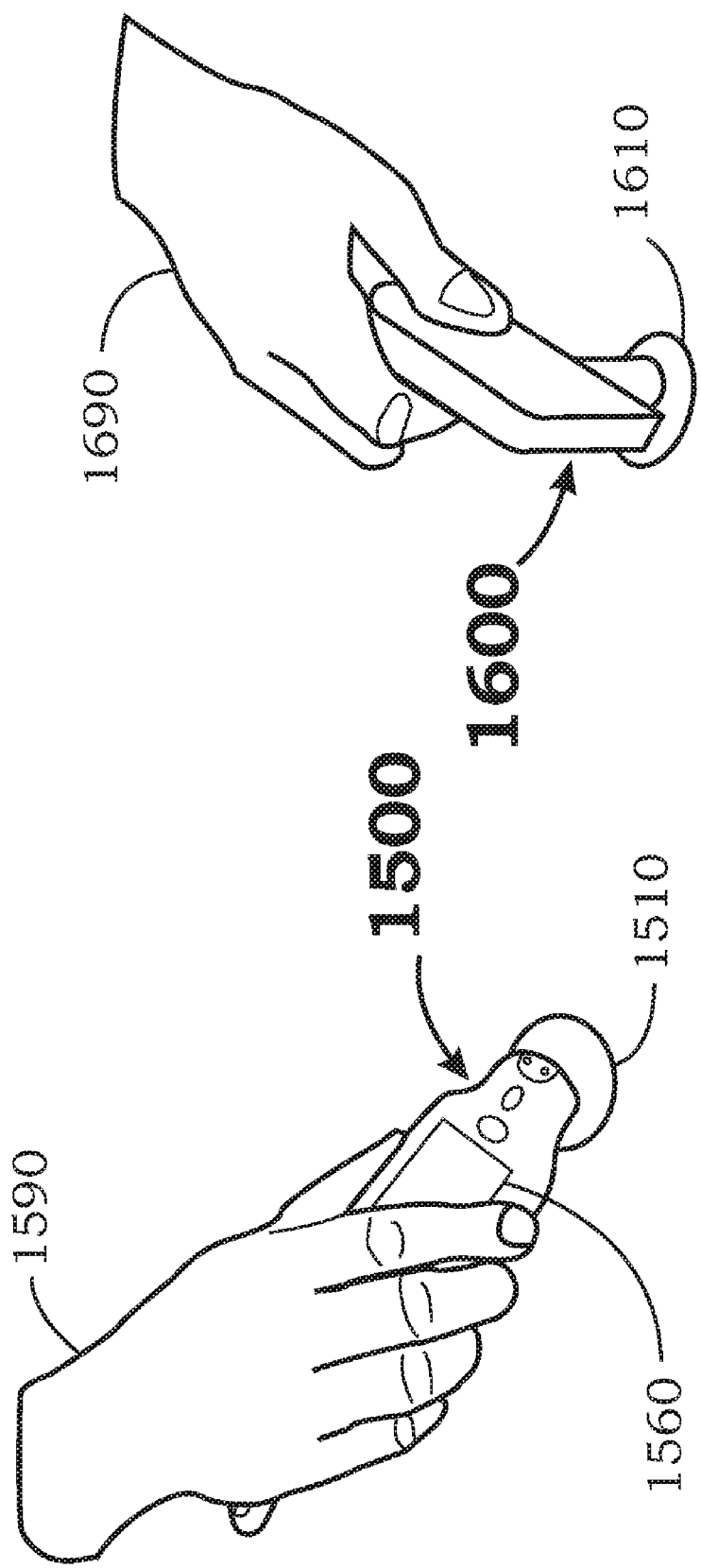

SYSTEMS AND METHODS FOR ANALYSIS AND DISPLAY OF HEART SOUNDS

BACKGROUND OF THE INVENTION

This invention relates generally to medical electronic devices for analysis of auscultatory cardiac sounds. More particularly, this invention relates to a method for recording, analyzing and audiovisual representation of heart sounds at the point of care, in humans, to enable differential diagnosis.

Auscultatory sounds have long been the primary inputs to aid in the detection of various physiological conditions. For instance the stethoscope is the primary tool used by a clinician to monitor heart sounds to detect and diagnose the condition of a subject's heart. Auscultation itself is extremely limited by a number of factors. It is extremely subjective and largely depends on the clinician's expertise in listening to the heart sounds and is compounded by the fact that certain components of the heart sounds are beyond the gamut of the human ear. In addition, auscultation relies on correctly determining which of the primary heart sounds correspond to the systole diastolic phase of the heart. This is made more difficult when ectopic beats occur.

A number of improvements have been developed to circumvent such bottlenecks, ranging from relatively noise-free electronic auscultation, to complex computer algorithms that can analyze the cardiac sounds, calculate various numerical values like heart rate, ascertain the heart sound phases etc. For example, algorithms are available that allow heart sounds in electronic format to be visualized on a personal computer screen and analyzed.

Accordingly, personal computer (PC) based auscultatory devices like the Acoustic Cardioscan from Zargis Medical Corporation of Stamford, Conn., and software packages like the Veteran Phonocardiograph monitor from BioSignetics Corporation of Exeter, N.H., are capable of a wide range of operations and manipulations of heart sounds offline. However, the above described PC based platforms suffer from the following shortcomings and bottlenecks. These PC based systems call for a separate data gathering device to record heart sounds in the format that can be processed by the PC based algorithm. In addition, there is a critical time delay between the time the clinician auscultates the subject and the time the clinician applies the PC based analysis to the recorded heart sounds. There are also portability issues associated with the PC based system setup.

Currently, handheld auscultatory devices have been developed in an attempt to circumvent some of the above described problems with PC based computer systems. These handheld devices do incorporate the data gathering mechanism in the device itself, obviating the need for separate data gathering. Handheld devices sold under the brand names Cadiscope (from Caditec AG Medical Instruments of Switzerland) and the Visual Stethoscope (from MC21 Meditech Group) are instances of such handheld auscultatory devices. However handheld devices have their own shortcomings. For example, some handheld devices are designed such that the chest piece is housed in the device itself thereby rendering sterilization processes difficult, or at least call for involved and expensive methods of cleaning. Further, the mere display of the heart sounds or ECG signals, in addition to the audio of the heart sounds is insufficient for the user to ascertain the condition of the heart.

It is therefore apparent that an urgent need exists for an improved auscultatory device that is easy to use, accurate, portable, cost-effective and easy to sterilize and maintain.

SUMMARY OF THE INVENTION

To achieve the foregoing and in accordance with the present invention, a method and system of analyzing and displaying heart sounds is provided. Such an auscultation system is useful for a clinician to efficiently and cost-effectively auscultate patients.

In one embodiment, the auscultation system includes a sensor for sensing heart sounds from at least one chest location of the patient and for transducing the heart sounds into electrical signals. The auscultation system also includes a signal processor for selectively filtering the electrical signals thereby highlighting frequency differences of the heart sounds, and further includes a video display for selectively displaying the selectively filtered electrical heart signals.

The auscultation system aids the clinician's diagnosis of the heart sounds by visually displaying at least an S1 heart sound and an S2 heart sound, and ascertaining an onset of at least one of the heart sounds. A corresponding audio representation of the heart sounds can be provided to the clinician.

In some embodiments, in addition to displaying the heart sounds, the auscultation system also displays calipers corresponding to the time domain and the frequency domain of the heart sounds, permitting the clinician to zoom in and out portions of the heart sounds of particular interest and also to take more accurate measurements of these portions of the heart sounds.

These and other features of the present invention will be described in more detail below in the detailed description of the invention and in conjunction with the following figures.

BRIEF DESCRIPTION OF THE DRAWINGS

In order that the present invention may be more clearly ascertained, one embodiment will now be described, by way of example, with reference to the accompanying drawings, in which:

FIGS. 10A-10G show screenshots illustrating the various functions of the auscultation device of FIG. 1.

FIGS. 15 and 16 show embodiments of the auscultation device of FIG. 1 wherein the heart sound signal acquirer is attached directly to the main body of the auscultation device.

DETAILED DESCRIPTION OF THE INVENTION

The present invention will now be described in detail with reference to several embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention. The features and advantages of the present invention may be better understood with reference to the drawings and discussions that follow.

Figure 1:
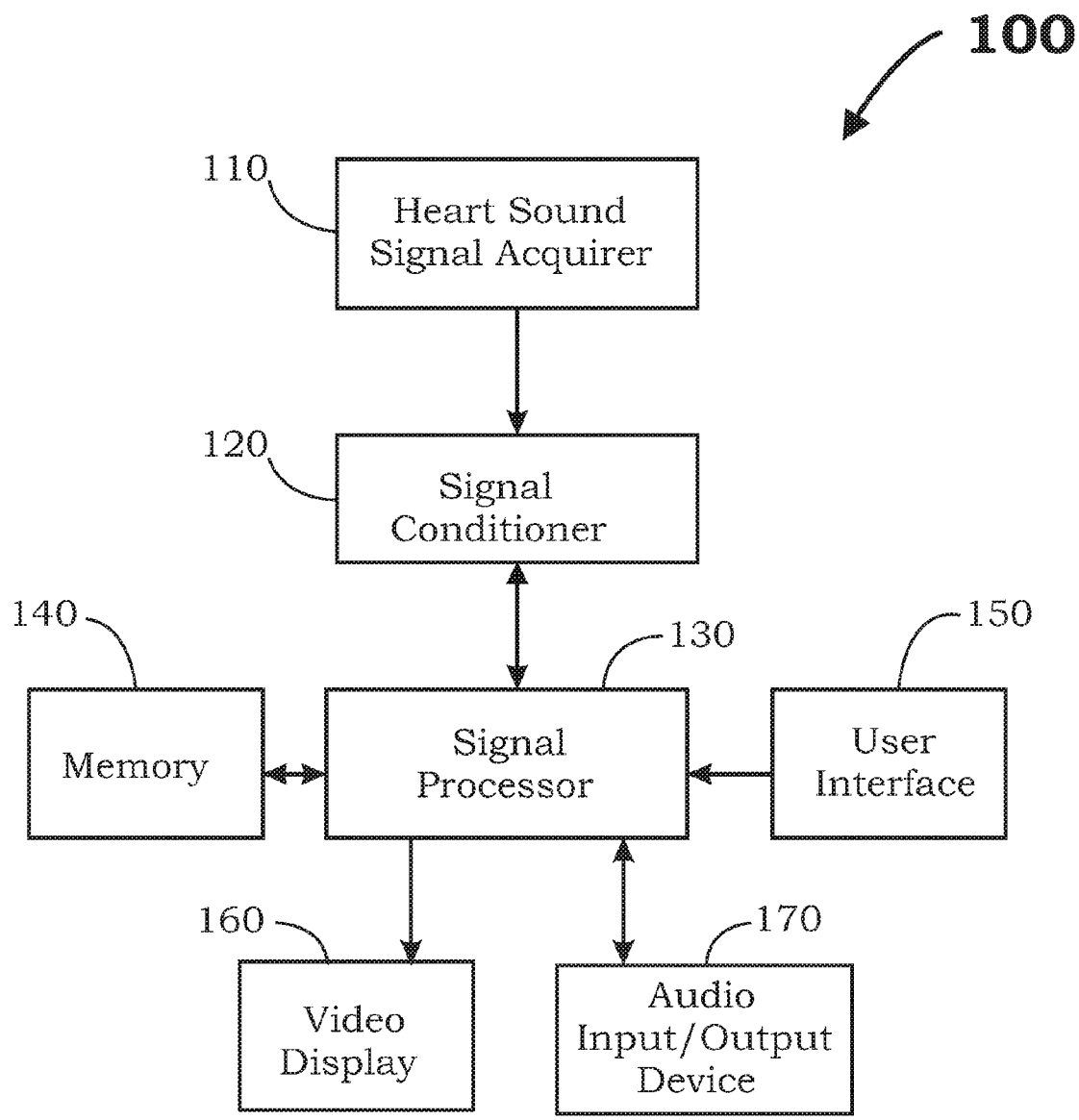
FIG. 1 is a block diagram showing one embodiment of an auscultation device for analyzing and displaying heart sounds in accordance with the present invention.

To facilitate discussion, FIG. 1 is a block diagram showing one embodiment of an auscultation device 100 for analyzing and displaying heart sounds in accordance with the present invention. Device 100 includes heart sound signal acquirer 110, signal conditioner 120, signal processor 130, memory 140, user interface 150, video display 160 and audio input/output device 170.

Memory 140 can be fixed or removal memory, and combinations thereof. Examples of suitable technologies for memory 140 include solid-state memory such as flash memory, or a hard disk drive.

User interface 150 can be a keypad, a keyboard, a thumbwheel, a joystick, and combinations thereof. Video display 160 can be an LCD screen, or can be an LED display or a miniature plasma screen. It is also possible to combine video display 160 with user interface 150 by use of technologies such as a touch screen. Contrast and brightness control capability can also be added to display 160.

Audio input/output (I/O) device 170 includes a microphone, and speakers, earphones or headphones, any of which can be internal or external with respect to device 100. It is also possible to use wireless audio I/O devices such as a Bluetooth-based headset. Volume control of device 170 can also be provided.

Figure 2:
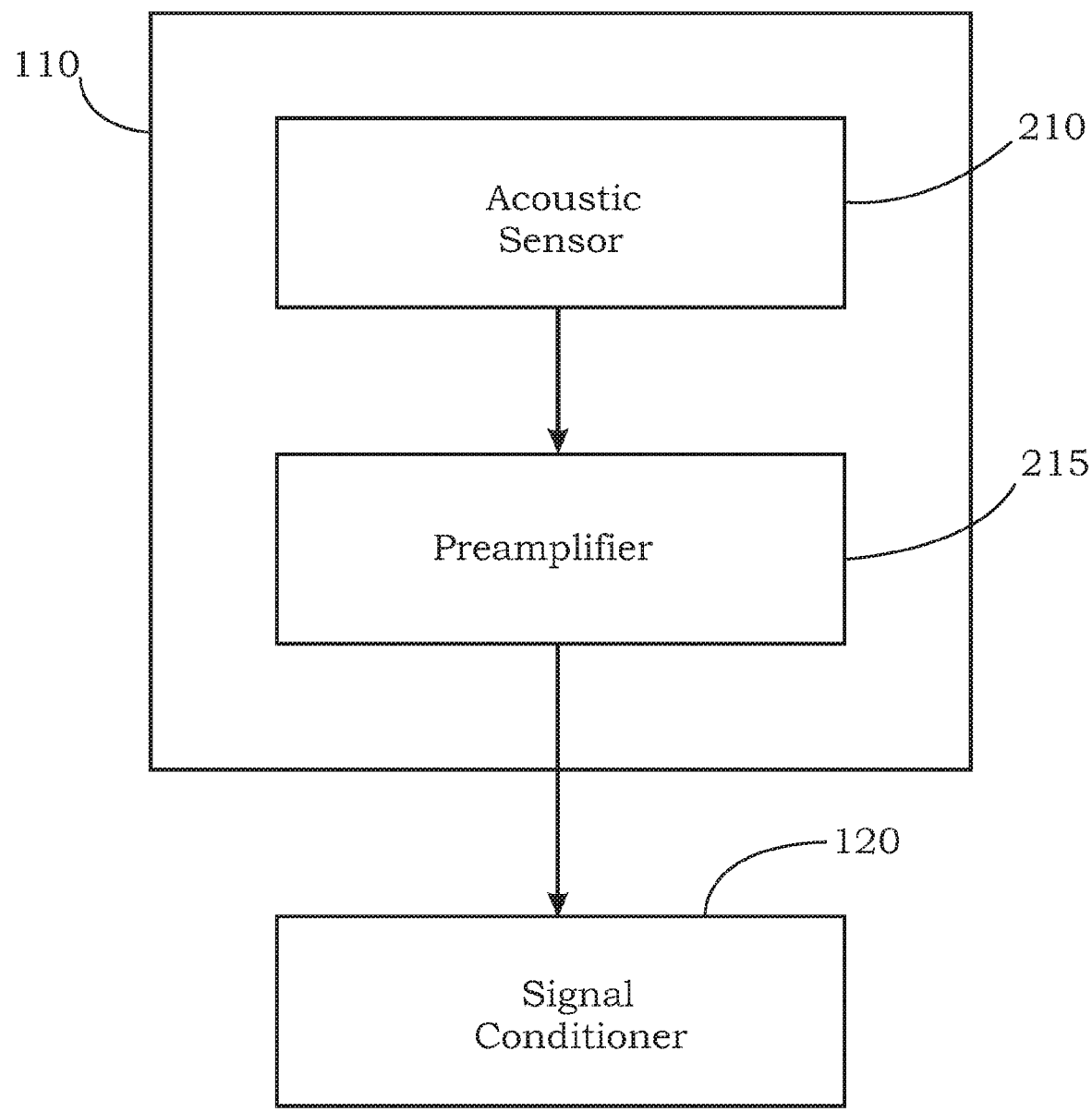
FIG. 2 is a block diagram illustrating a heart sound signal acquirer for the auscultation device of FIG. 1.

FIG. 2 is a block diagram illustrating heart sound signal acquirer 110 in greater detail. Acquirer 110 includes an acoustic sensor 210 and a preamplifier 215 which are coupled to signal conditioner 120. In this embodiment, sensor 210 is a unidirectional microphone housed in a chest piece assembly. Preamplifier 215 is solid-state and provides pre-amplified heart sounds to signal conditioner 120.

Figure 3:
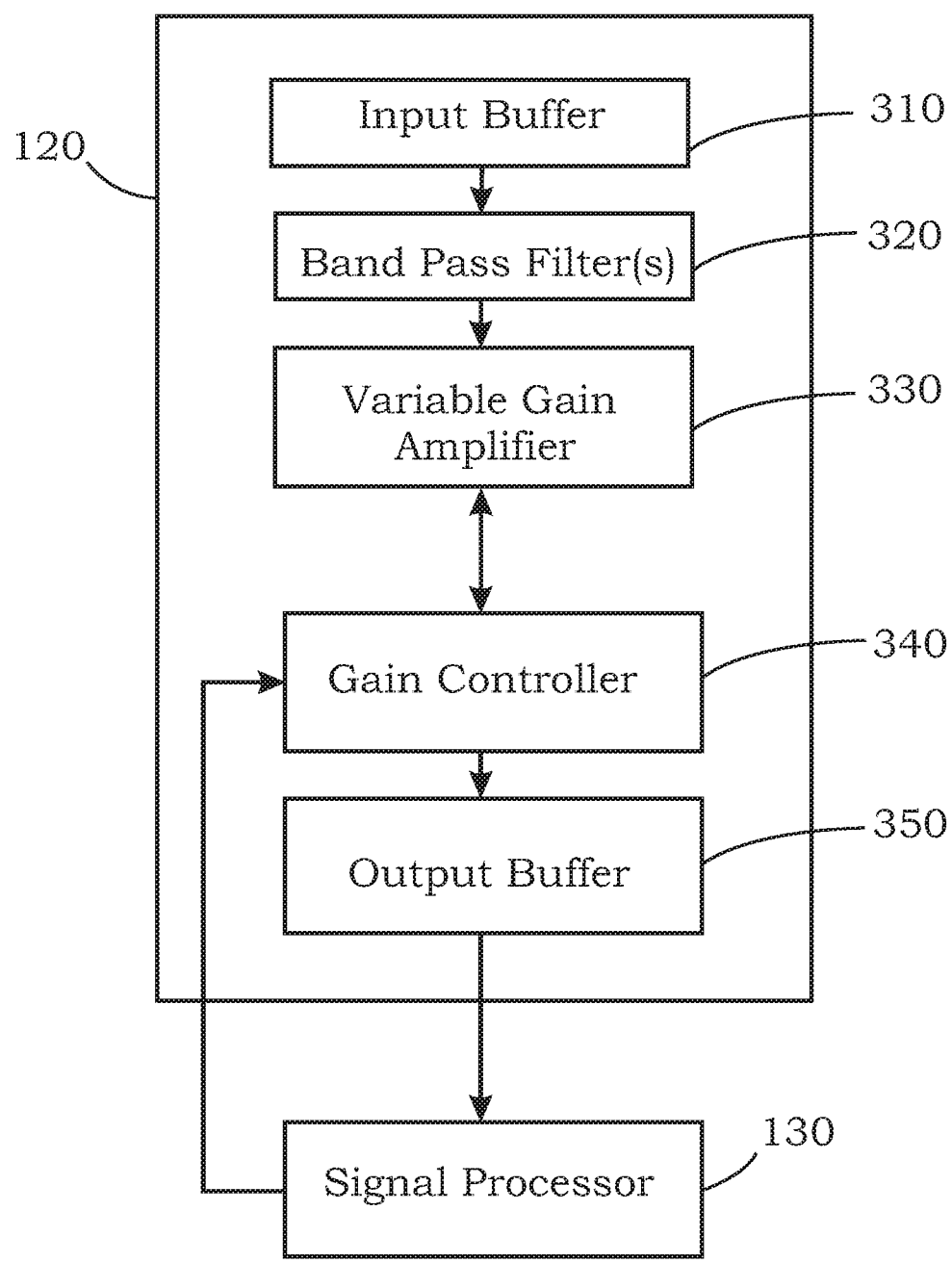
FIG. 3 is a block diagram illustrating a heart sound signal conditioner for the auscultation device of FIG. 1.

FIG. 3 is a detailed block diagram illustrating heart sound signal conditioner 120 which includes an input buffer 310, one or more band pass filter(s) 320, a variable gain amplifier 330, a gain controller 340 and an output buffer 350. Output buffer 350 is coupled to signal processor 130 which in turn is coupled to gain controller 340.

In this embodiment, filter 320 is a $4^{th}$ order Butterworth pass band of 5 Hz to 2 kHz which limits the analysis of the heart sound signal to frequencies less than 2 kHz, thereby ensuring that all frequencies of the heart sounds are faithfully captured and at the same time eliminating noise sources that typically exist beyond the pass band of filter 320. Variable gain amplifier 330 of signal conditioner 120 serves to vary the signal gain based on a user-selectable input parameter, and also serves to ensure enhanced signal quality and improved signal to noise ratio. The conditioned heart sound signal after filtering and amplification is then provided to signal processor 350 via output buffer 350.

Figure 4:
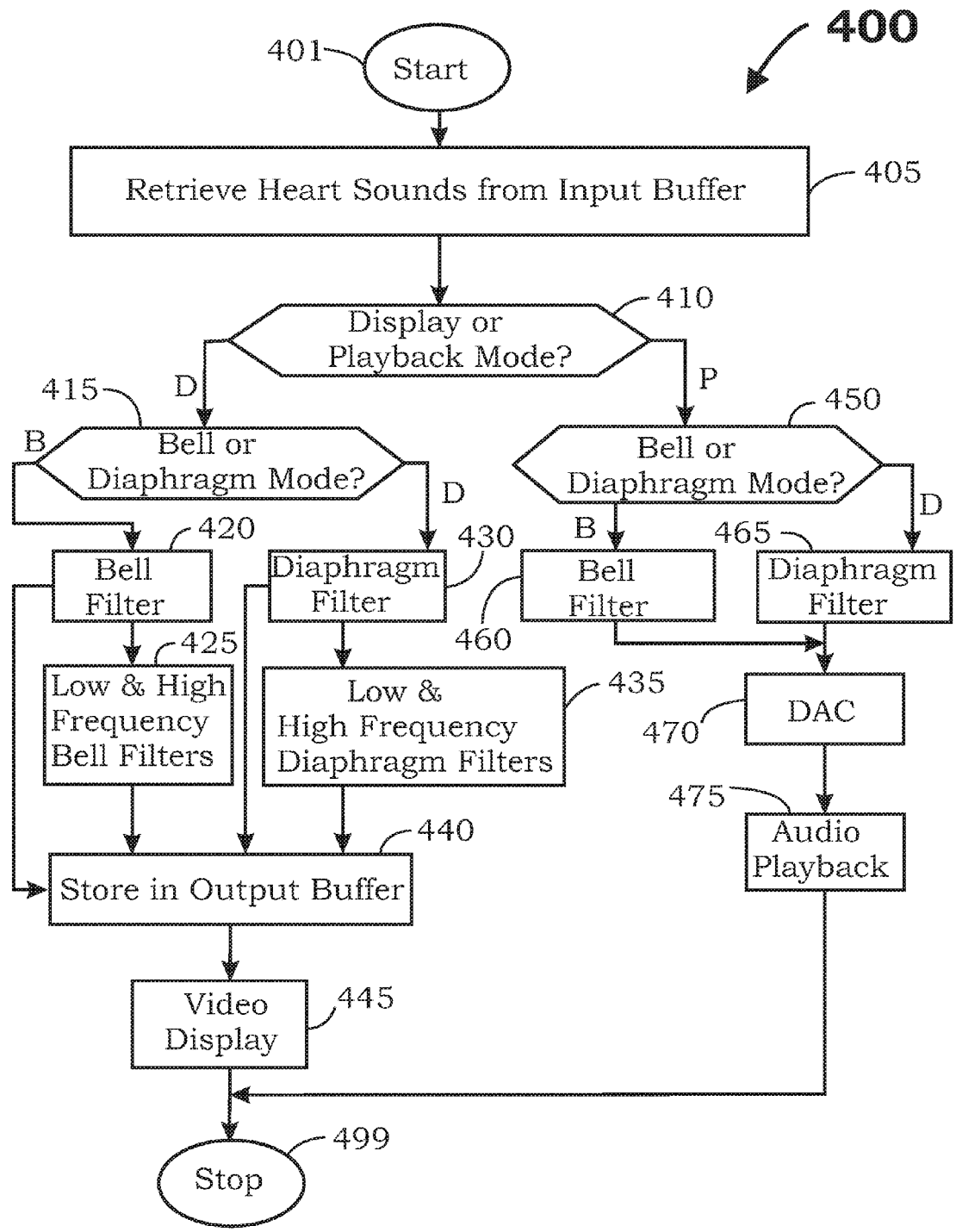
FIG. 4 is a flow diagram illustrating heart sound signal decomposition for the auscultation device of FIG. 1.

FIG. 4 is a flow diagram illustrating an exemplary "Decomposition" of heart sound signals by one embodiment of signal processor 350. In step 405, heart sound signals are retrieved from input buffer 310. Using the appropriate key sequence on user interface 150, the user can select Visual Display mode and/or Audio Playback mode as shown in step 410.

Two sets of filters of different frequencies pass bands pertain to two modes of operation, namely, a "Bell" mode and a "Diaphragm" mode. These two operational modes emulate the respective functions of a combined Bell/Diaphragm head found in traditional acoustic (non-electronic) stethoscopes that many experienced clinicians are accustomed to using. These two sets of filters pertain to audio filtering as shown in steps 460 and 465, as well as video filtering for subsequent visual display on display 160. Depending on the user selection between audio playback mode and visual display mode, the pertinent set of audio or video filters is enabled.

As shown in step 415, the user's visual analysis of the decomposed the heart sounds is based on the Bell or Diaphragm mode selected through user interface 150. Referring also to FIG. 10F which shows an exemplary "Bell" Visual Display mode, the composite heart sound signal which is between 0-300 Hertz is decomposed into two component frequency ranges; a low frequency component between 0-150 Hertz and a high frequency component between 100-300 Hertz (steps 420, 425). The low frequency components highlights S1, S2, S3, S4, and low frequency murmurs, while the high frequency components highlights S1, S2, low frequency murmurs (prominent) and medium frequency murmurs (suppressed).

In FIG. 10D which illustrates a "Diaphragm" Visual Display mode, the composite heart sound signal which is between 60-800 Hertz is also decomposed into two component frequency ranges, a low frequency component between 60-300 Hertz and a high frequency component between 250-800 Hertz (steps 430, 435). The low frequency components highlighting the S1, S2, medium frequency murmurs (prominent) and low frequency murmurs (suppressed). The high frequency components highlighting the medium frequency murmurs and high frequency murmurs.

In this embodiment, the frequencies captured in "Bell" mode include the complete range of Bell frequencies. Similarly the frequencies captured in "Diaphragm" mode include the complete range of the Diaphragm frequencies. Other customized decomposition modes with user definable component frequency ranges are also possible. As discussed above, display 160, e.g., an LCD display, provides the visual representation of the heart sounds to the user by storing the waveforms in output buffer 350 prior to visual display (steps 440, 445). Meanwhile audio output device 170, e.g., a set of headphones, provides an auditory representation of the same heart sounds to the user by a digital-to-analog conversion (DAC) prior to audio playback (steps 470, 475). Preferably, both visual and auditory representations of the heart sounds as experienced by the user are synchronized.

In another embodiment, the sensor head has two opposing sensors (not shown), i.e., a Bell-side sensor and a Diaphragm-side sensor, like a traditional acoustic stethoscope. Accordingly, instead of the user manually selecting the Decomposition mode, device 100 automatically selects the appropriate decomposition mode by sensing whether the Bell side sensor or the Diaphragm side sensor of the sensor head is touching the chest wall of the patient and hence is generating a stronger heart sound signal. The heart sounds are then analyzed by the corresponding Bell or Diaphragm filters which are also automatically selected by processor 130.

Figure 11B:
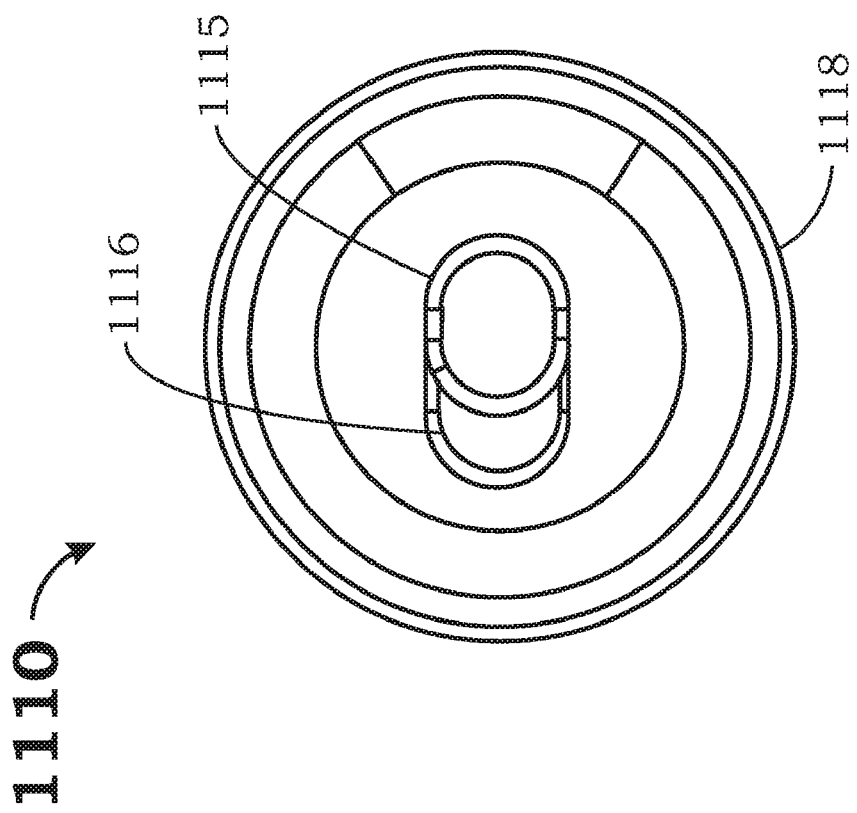
FIGS. 11A & 11B are isometric and top views, respectively, of another embodiment of a heart sound signal acquirer for the auscultation device of FIG. 1.
Figure 11A:
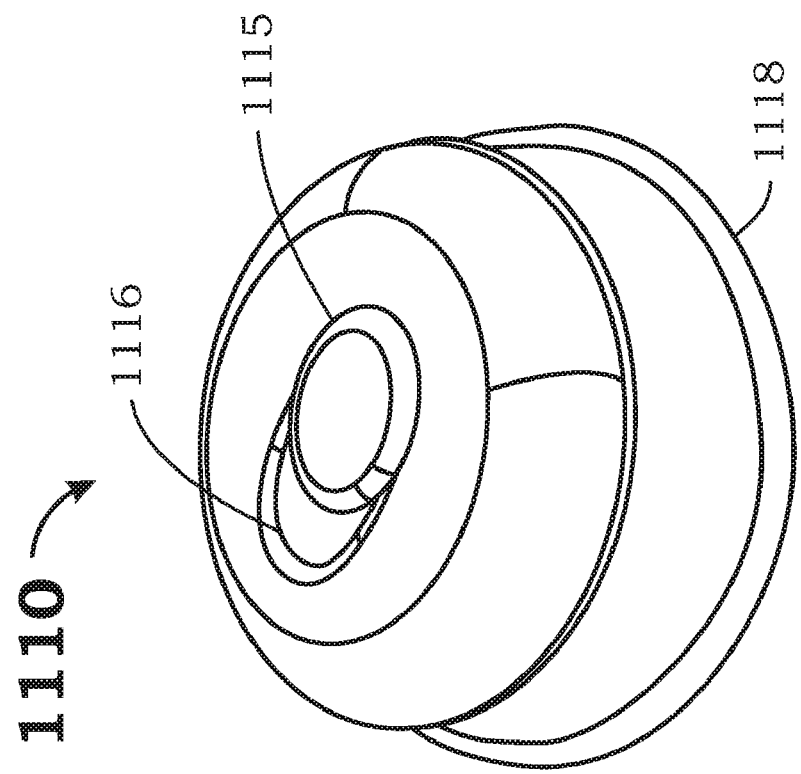

In yet another embodiment illustrated by the isometric and top views of FIGS. 11A and 11B, respectively, heart signal acquirer 1110 also includes a selector switch 1115 which the user can use to select from two or more pre-determined modes, e.g., a "Bell" mode or a "Diaphragm" mode, using a finger of the same hand that is hold signal acquirer 1110 against the chest wall of the patient. While an exemplary two-position slider switch assembly 1115, 1116 is shown, it is understood that other selector switches are also possible, including push button switches, rocker switches and rotary switches. Switch 1115 can be located on the top of or on the side of signal acquirer 1110.

Figure 5:
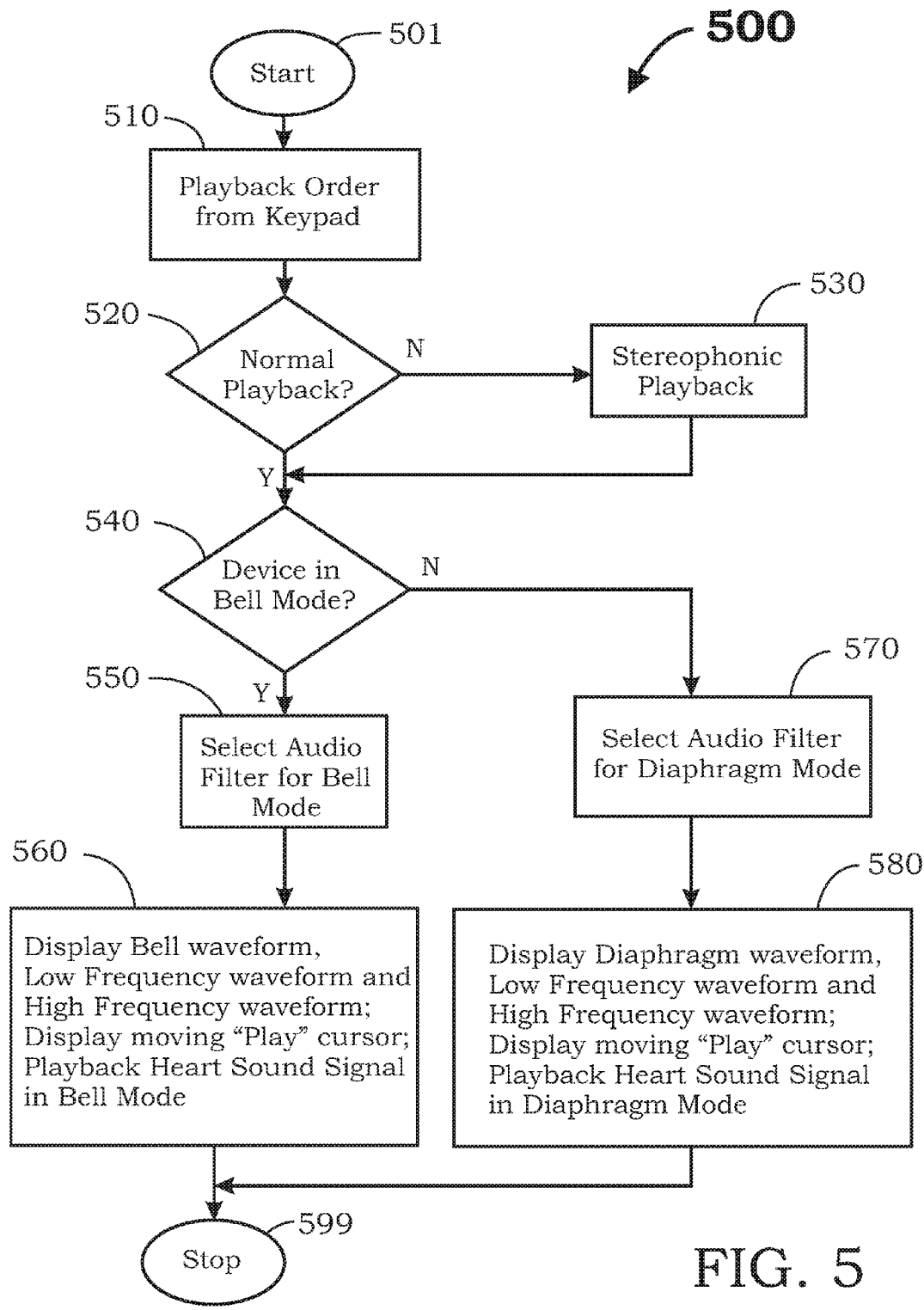
FIG. 5 is a flow diagram illustrating heart sound signal playback for the auscultation device of FIG. 1.

Referring now to FIG. 5, which is a flow diagram illustrating heart sound signal audio playback as facilitated by the user inputting the "Playback" command using user interface 150, such as a keypad (step 510). In the Playback function, the user can select "Normal" playback or "Stereophonic" playback (steps 520, 530). The user can also select "Bell" mode or "Diaphragm" mode (steps 550, 570). In step 560, when Bell mode has been selected, display 160 such as an LCD screen, shows the composite Bell waveform as well as the respective component low frequency and the high frequency waveforms. Similarly, in step 580, when Diaphragm mode has been selected, display 160 such as an LCD screen, shows the composite Diaphragm waveform as well as the respective component low frequency and the high frequency waveforms.

As shown in FIG. 10G, a vertical "Play" cursor scrolls across the three waveforms on display 160 synchronously with the audio playback described above, thereby ensuring that the user can visually see on display 160 what he/she is hearing via audio output device 170.

Figure 6:
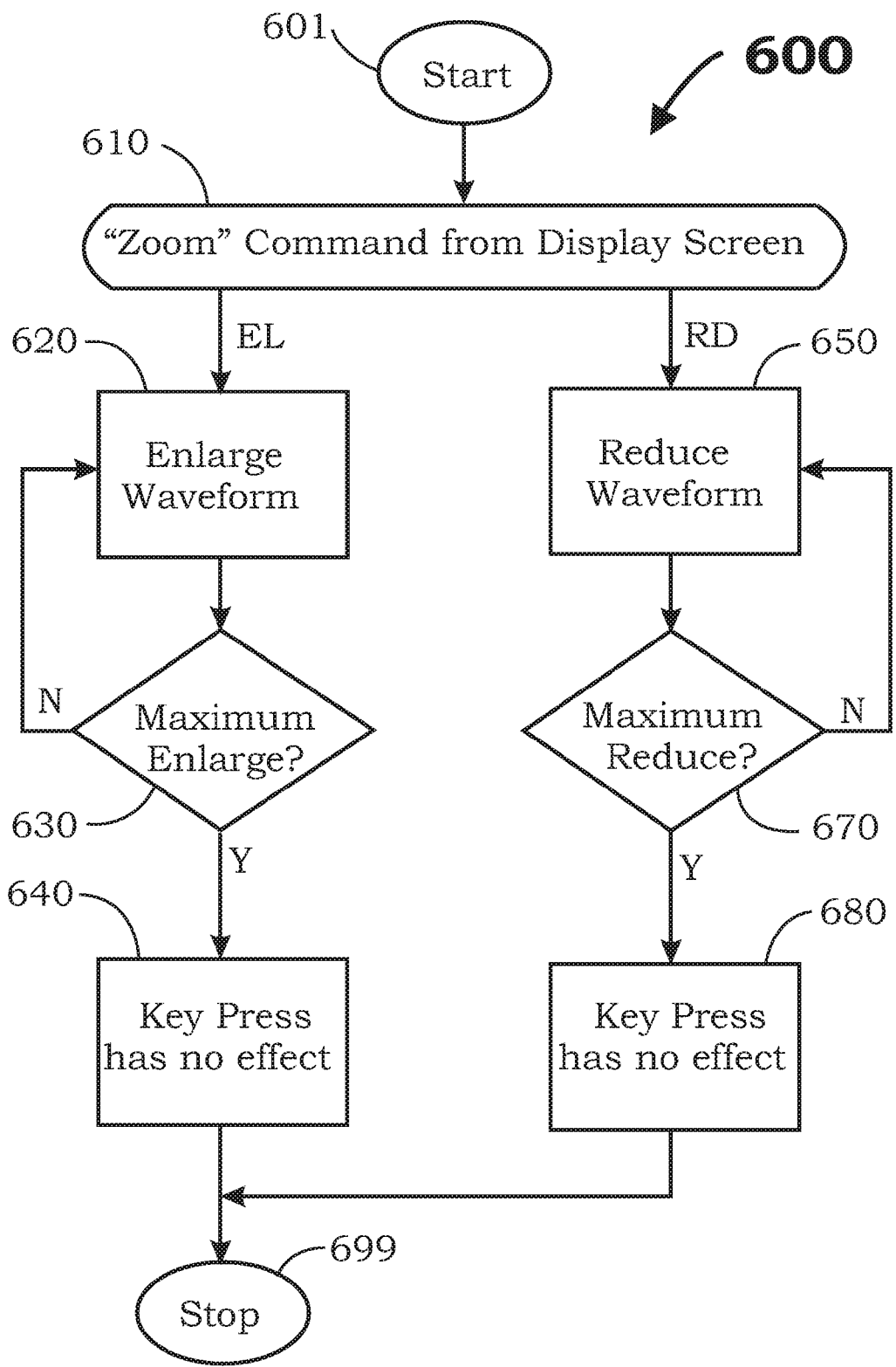
FIG. 6 is a flow diagram illustrating display zooming for the auscultation device of FIG. 1.

FIG. 6 is a flow diagram illustrating the "Zoom" command for video display 160 of auscultation device 100. By selecting the Zoom command using user interface 150, the user is able to Enlarge or Reduce the heart sound waveforms along the horizontal-axis, i.e., along the time domain, displayed on video display 160 (step 610). When enlarging, the Enlarge key press will have no effect once the maximum Enlargement has been reached (steps 620, 630, 640). Similarly, when reducing, the Reduce key press will have no effect once the maximum Reduction has been reached (steps 650, 670, 680).

Figure 7:
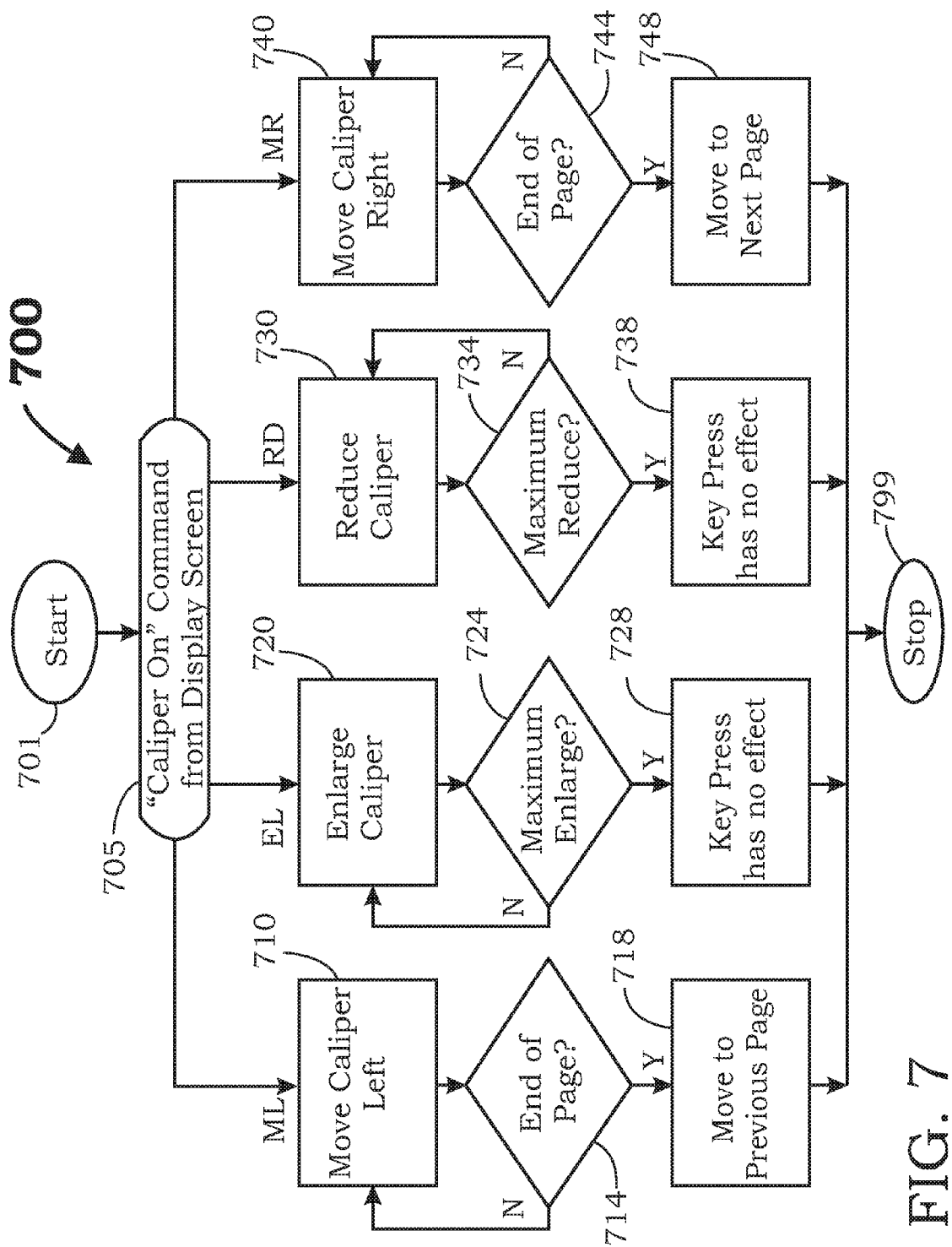
FIG. 7 is a flow diagram illustrating display calipers for the auscultation device of FIG. 1.

FIG. 7 is a flow diagram illustrating soft "Calipers" for time measures of heart sound waveforms. The user activates the Caliper function on video display 160 by pressing keys on user interface 150, causing soft calipers to appear on display 160 as a pair of lines (step 705). Along with both X and Y calipers, the time widths enclosed by the respective calipers also appear on display 160.

Referring also to FIG. 10E, if "X" calipers are selected, a pair of vertical calipers appears. X calipers allow the user to make accurate measurements of the time periods of the different heart sound phases. Conversely, as shown in FIG. 10F, if "Y" calipers are selected, a pair of horizontal calipers appears. Y calipers allow the user to ascertain the murmur grades, whenever murmurs are detected in the heart sounds.

The user is able to ascertain pathologic heart conditions using device 100 because of most conditions can be associated with their respective characteristic frequencies and amplitude durations. For example under the right conditions, mitral value regurgitation can be diagnosed with approximately 60% certainty.

By pressing appropriate key on user interface 150, the calipers can be repositioned by moving left or right relative to its current position. For example, as shown in steps 710, 714, calipers can be repositioned to the left until the calipers are at the end of the page, thereby causing the "previous page" of the heart sound waveforms to appear on display 160 (step 718). Alternatively, the calipers can be repositioned to the right until the calipers are at the end of the page (steps 740, 744), thereby causing the "next page" of the heart sound waveforms to appear on display 160 (step 748). Other display positioning modes are possible. For example, it is also possible to move the display window by partial page increments or portions thereof.

In addition the calipers on display 160 can be resized by expanding or reducing the size of the calipers. In steps 720, 724, the calipers can be enlarged until a maximum size is reached, and further key presses will no longer have any effect (step 728). Similarly, the calipers can be reduced until a minimum size is reached, and further key presses will no longer have any effect (steps 730, 734, 738).

Figure 8:
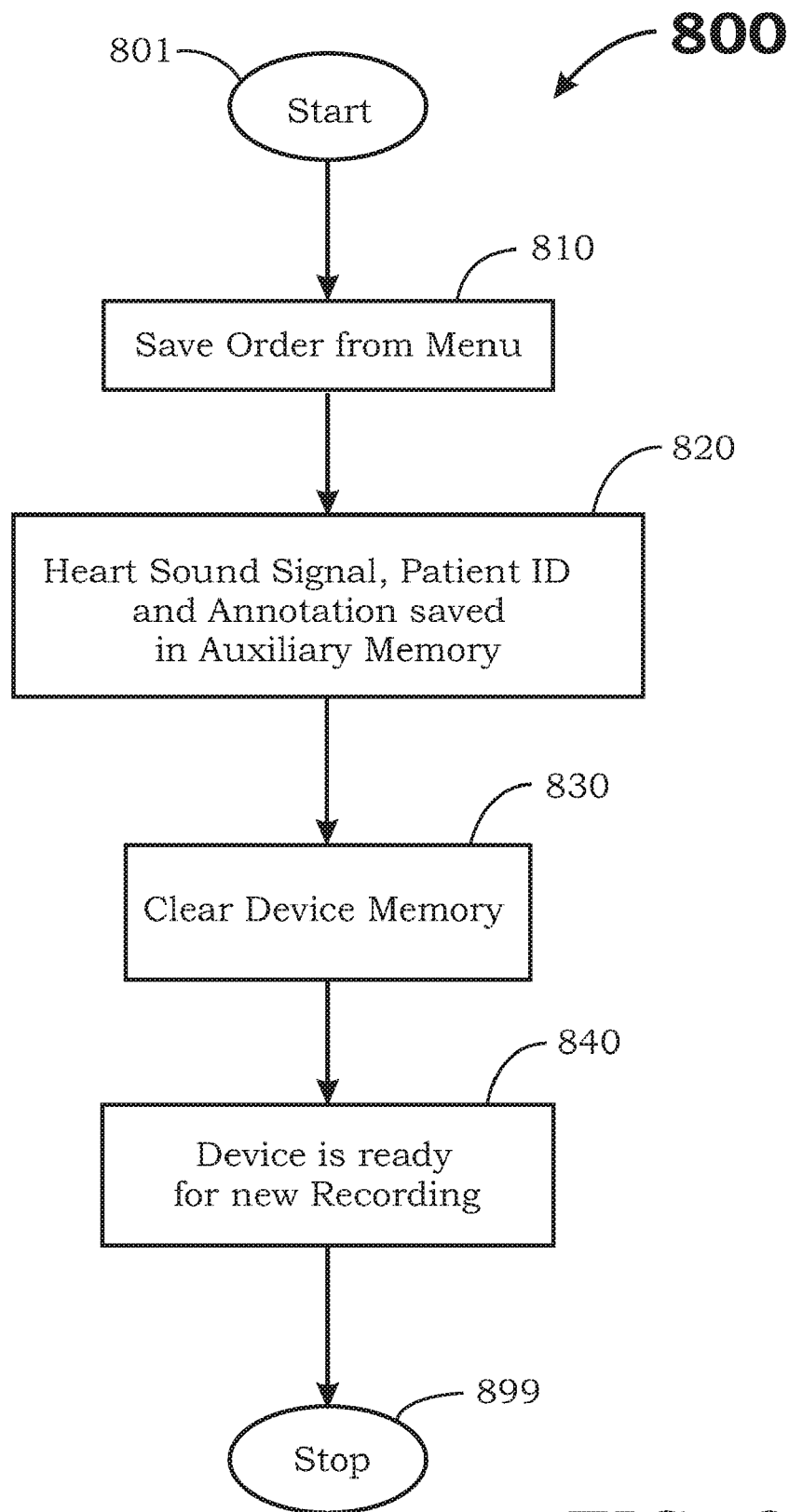
FIG. 8 is a flow diagram illustrating heart sound signal storage for the auscultation device of FIG. 1.

FIG. 8 is a flow diagram illustrating the storage of heart sound signals acquired by auscultation device 100. In step 810, the user selects the "Save" function by pressing keys on user interface 150, causing device 100 to download the heart sound signal, and associated patient identification and any annotation into a removable or an external memory device (step 820). In this embodiment, the patient ID and annotations can be added using voice recordings thereby minimizing the need for additional keystrokes. The local memory of device 100 can now be freed up for recording new heart sound signals (steps 830, 840).

In some embodiments, speech recognition technology known to one skilled in the art can be incorporated into device 100, enabling a textual record of the patent identification and annotations to be included instead or in addition to an audio recording. Speech recognition capability can also be used to activate the various functions of device 100, thereby resulting in a user-friendly and relatively hands-free auscultation device. Accuracy and/or efficiency of speech recognition can be increased by limiting the vocabulary and/or training the synthesizer to recognize the user's vocal characteristics.

It is also possible to incorporate speech synthesis capability into device 100 so as to enhance the ease of use with prompts, instructions and/or feedback. For example, device 100 can ask a user whether device 100 should be sensing in "Bell" or "Diaphragm" mode, or to inform the user that an invalid command/mode has been selected.

Figure 9:
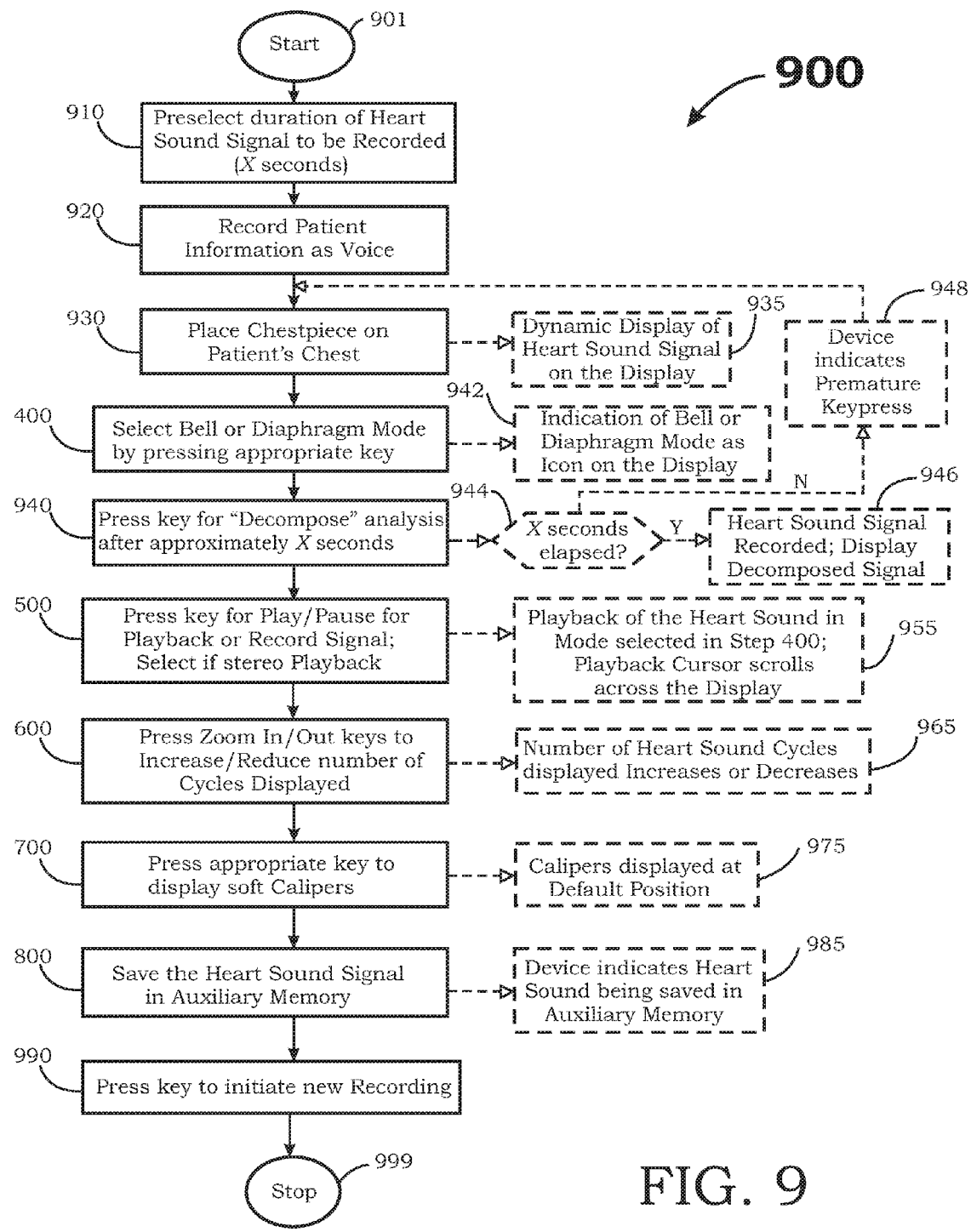
FIG. 9 is a flow diagram illustrating various functions of the auscultation device of FIG. 1.

Having described several of the functions of auscultation device 100 in detail, the flowchart of FIG. 9 and the screenshots of FIGS. 10A-10G are now used to illustrate a typical sequence of the various functions that a user may activate while using auscultation device 100 to diagnose the heart sounds of a patient.

Figure 10A:
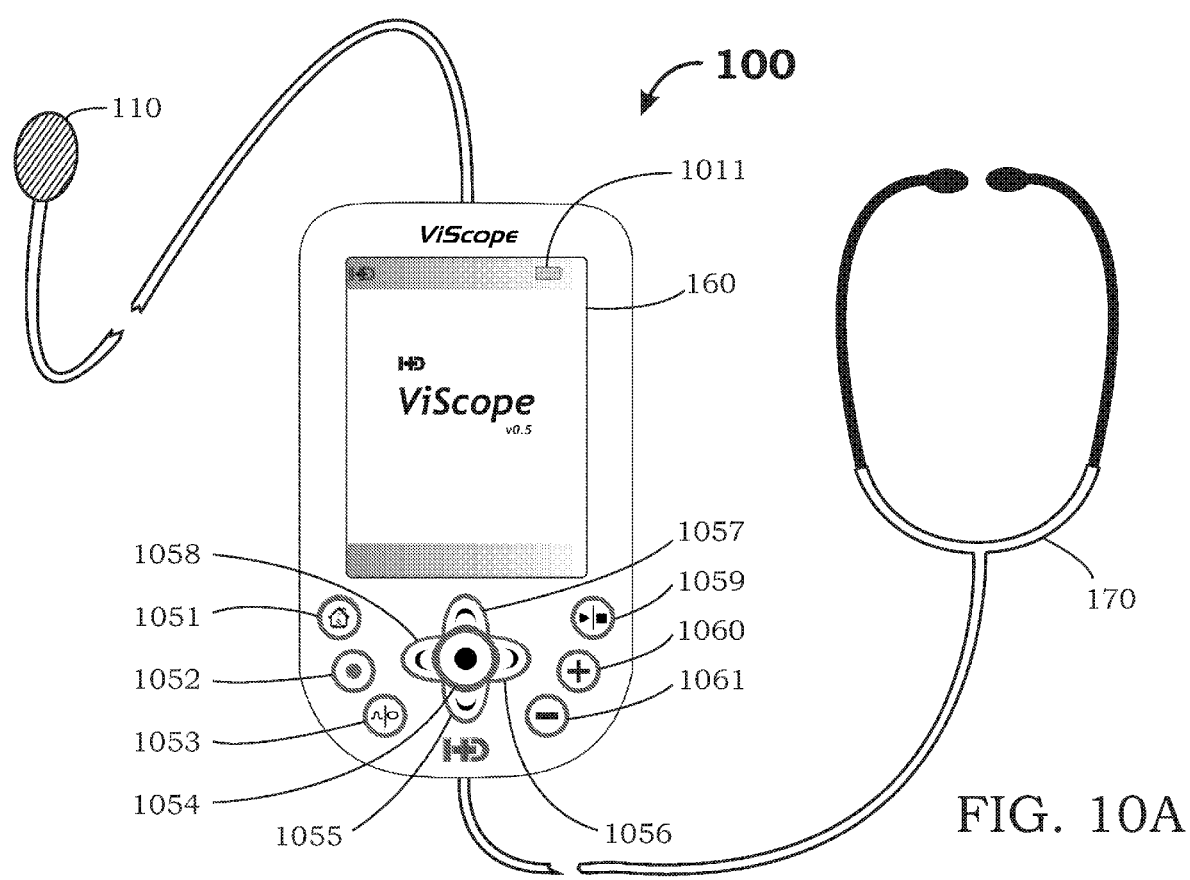

In one embodiment as shown in FIG. 10A, a heart sound signal acquirer 110, e.g., a microphone embedded in a chestpiece, and audio input device 170, e.g., earphones, are electrically coupled to signal processor 130 of device 100. The user turns device 100 on by pressing the "Function Select" key 1054. FIG. 10B shows device 100 during the "Power On" cycle, while FIG. 10A shows battery level 1011 upon completion of the "Power On" which enables the user to keep track of the power needs of device 100.

To conserve power, device 100 goes into a sleep mode if there are no key presses after a timeout period, e.g., after two minutes. While in this sleep mode, any key press causes device 100 to return to the last state of operation.

The user pre-selects a suitable duration of heart diagnosis, e.g., X seconds, of heart sound signals to be acquired (step 910). As illustrated by FIG. 10C, device 100 displays function "Acquire" 1013 and enables the user to make a voice recording of the associated patient information including patient ID (step 920). The user places chestpiece 110 on the patient's chest (step 930), which causes device 100 to output the heart sound 1064 on video display 160 as shown in FIG. 10C (device response 935).

Together with the user's training and experience, the "Original" heart sound 1064 enables the user to interpret the graphical representation of the complete heart waveforms, thereby providing the user with a general idea of the condition of the patient's heart. Note that device 100 initially displays the default audio volume level as an adjustable "Speaker" icon 1012, the default signal gain level as a "Dial" icon 1016, and the default zoom as a "Percentage" icon 1015 on video display 160.

In step 400, the user selects "Bell" or "Diaphragm" mode by pressing "Mode Select" key 1053, thereby causing device 100 to indicate the appropriate mode, in this example, "Diaphragm" 1014, on video display 160 (device response 942). Referring now to FIG. 10D, when the user presses "Function Select" key 1052 to activate the "Decompose" function (step 940), which is followed by a lapse of X seconds, original heart sound 1067, and decomposed low frequency heart sound 1066 and high frequency heart sound 1065 are displayed by device 100 (device responses 944, 946). The decomposed heart sounds 1065, 1066 enable the user to identify the various heart sound phases and also to detect the presence of heart murmurs.

By manipulating the "Play/Pause" key 1059 as shown in step 500, the user causes device 100 to playback and/or record the heart sound signal, and also enables the user to select between "Normal" and "Stereophonic" playback modes (device response 955).

Referring to FIG. 10E, by manipulating Function Select key 1054 and "Directional" keys 1055, 1057 (step 600), the user is able to "Zoom In" and "Zoom Out" on the heart sounds in the time domain, i.e., along the X-axis of display 160 (device response 965), thereby allowing the user to observe a closer expanded view of the heart sounds. In step 700, by activating "X-Calipers" 1072a, 1072b, device 100 enables the user to make more accurate time measurements of the heart sound phases (device response 975). This ability to zoom in/out and to measure the heart sounds in the time domain is particularly important when one of more of the heart sound phases exceed a particular "normal" time limit, and is indicative of a pathological condition.

Conversely, as shown in FIG. 10F, by manipulating Function Select key 1054 and Directional keys 1056, 1058, the user is able to activate and position "Y-Calipers" 1071a, 1071b to provide measurements of the heart sounds in the frequency domain, i.e., along the Y-axis of display 160, as illustrated by step 700 and device response 965. The ability to accurately measure the amplitude of the heart sounds facilitates the user to ascertain the grade of the murmurs, based on the width enclosed by the Y-Calipers.

FIG. 10G depicts device 100 during playback of the heart sounds, as indicated by "Playback" mode 1017 on display 160. Note vertical line cursor 1073 scrolls across display 160 during playback, synchronizing the video display with the audio playback of the heart sounds, and enabling the user to visually observing on display 160 what he or she is hearing on audio output device 170.

After playback, the user has the option of saving the heart sounds in memory 140 for future analysis before initiating a new recording by pressing "Home" key 1051 (step 800 and device response 985). The user can now initiate a new heart sound recording by pressing Function Select key 1054 as shown in step 900.

Figures 12A, 12B:
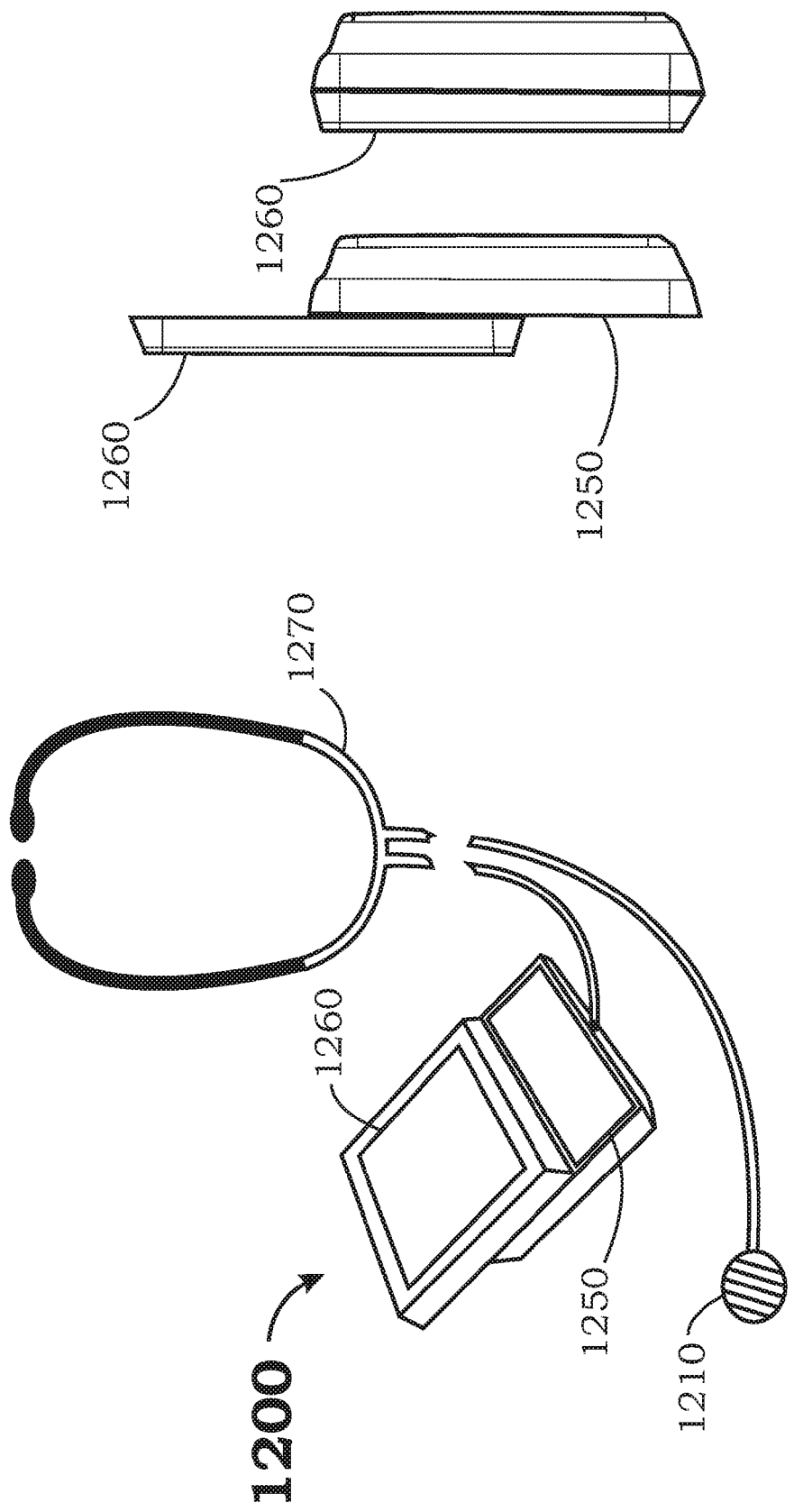
FIGS. 12A & 12B show an isometric and two side views of another embodiment of the auscultation device of FIG. 1.

FIG. 12A illustrates another embodiment 1200 in which heart sound acquirer 1210 and display 1260 are both coupled to audio input device 1270. FIG. 12B show side views of the "open" and "close" positions, respectively, of device 1200. The "power-on" function of device 1200 can be activated by sliding open device 1200 which simultaneously exposes user interface 1250. Conversely, sliding close device 1200 conceals user interface 1250 and powers-down device 1200.

Figure 13:
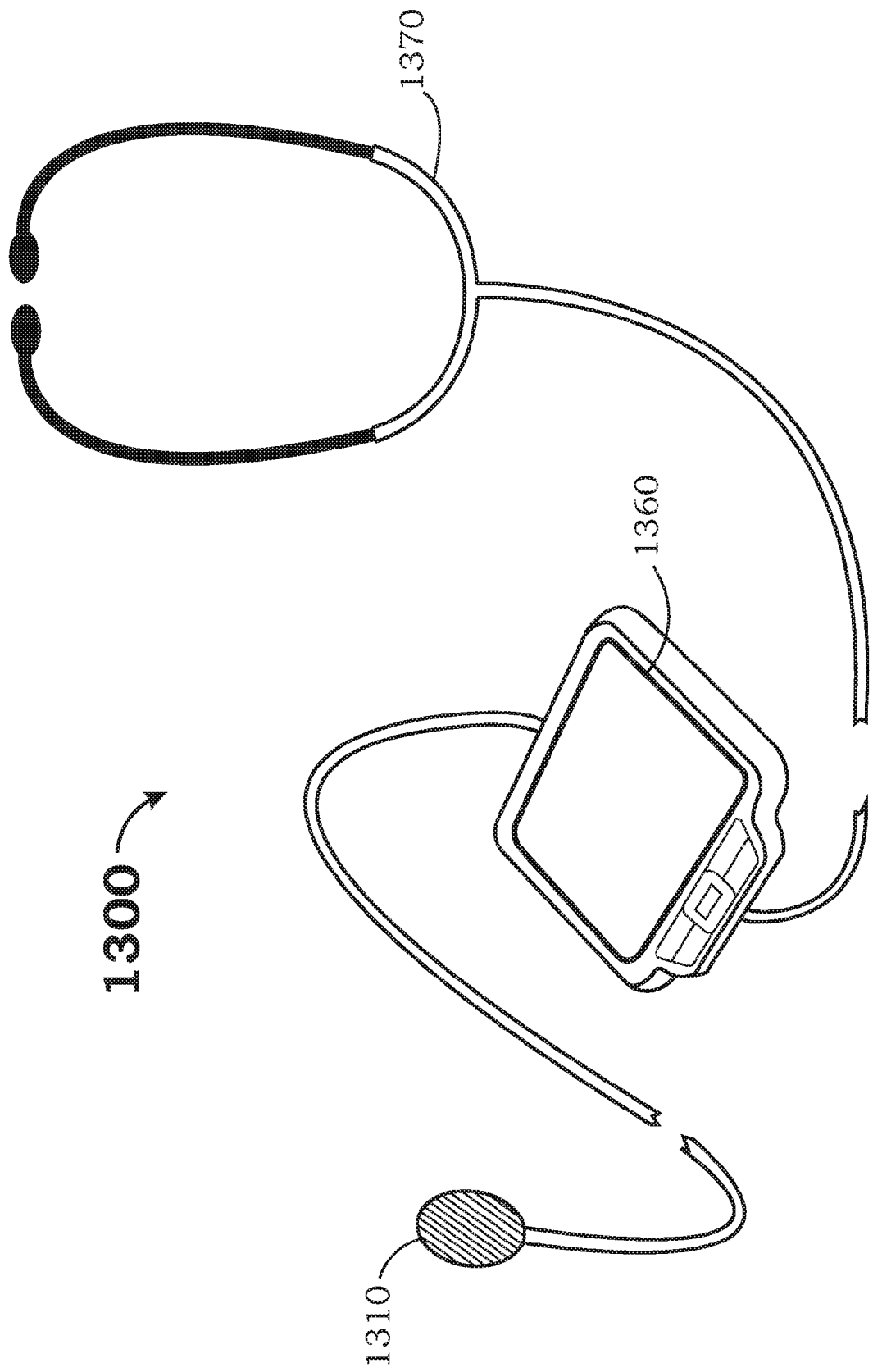
FIGS. 13 and 14 illustrate two additional embodiments of the auscultation device of FIG. 1.

FIG. 13 is an isometric view of an additional embodiment of device 100. Device 1300 includes a display 1360 which can be a touch-screen large enough to incorporate all or a portion of the user interface for device 1300. It is possible for device 1300 to be worn like a watch on the wrist of the user by adding a wrist strap.

Figure 14:
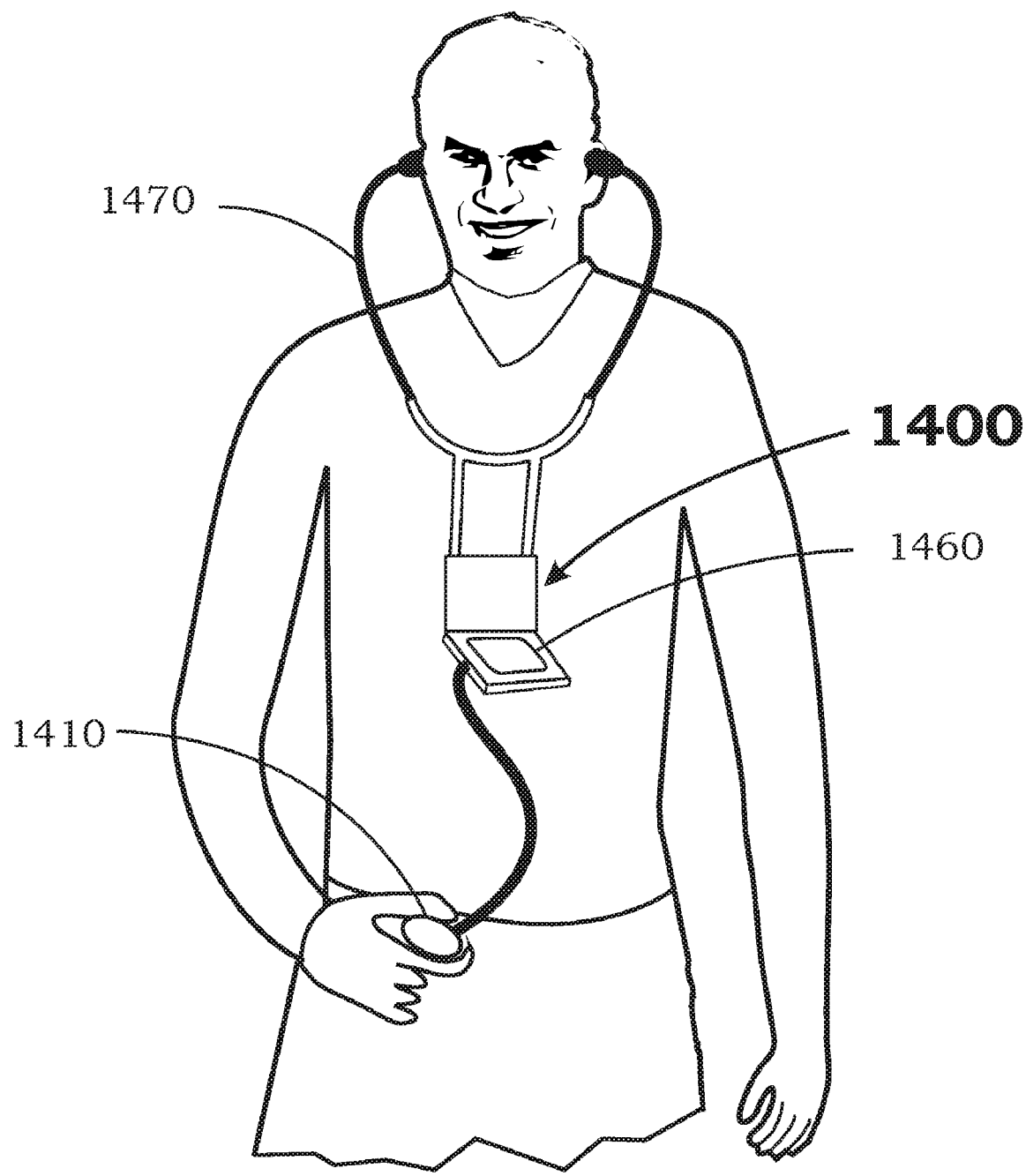

FIG. 14 is an isometric view of yet another embodiment of device 100. Device 1400 is a compact version with display 1460 supported by audio input device 1470. In addition, display 1460 of device 1400 can be conveniently flipped open resulting in a hands-free display capability. In this embodiment, heart sound acquirer 1410 is attached to display 1460.

Other modifications to device 100 are also possible. As shown in FIGS. 15, 16, it is also possible to incorporate sensors 1510, 1610 with devices 1500, 1600, respectively, resulting in very compact auscultation system designs. In addition to displaying the heart sounds, it is also possible for device 100 to generating gating signals S1, S2 for heart imaging systems. When tuned to appropriate frequencies, device 100 can also be used to sense and record lung sounds, including the higher frequency ranges associated with pulmonary problems such as wheezing.

In sum, device 100 provides many advantages over the existing auscultatory devices, including ease of use, accuracy, portability, cost-effectiveness and ease of sterilization and maintenance.

While the present invention has been described with reference to particular embodiments, it will be understood that the embodiments are illustrative and that the invention scope is not so limited. In addition, the various features of the present invention can be practiced alone or in combination. Alternative embodiments of the present invention will also become apparent to those having ordinary skill in the art to which the present invention pertains. Such alternate embodiments are considered to be encompassed within the spirit and scope of the present invention. Accordingly, the scope of the present invention is described by the appended claims and is supported by the foregoing description.

What is claimed is:

1. A method for displaying heart sounds of a patient, the method comprising:
    sensing heart sounds from at least one chest location of the patient;
    transducing the heart sounds into electrical signals;
    selectively filtering the electrical signals thereby highlighting frequency differences of the heart sounds, and wherein the selectively filtered electrical heart signals corresponds to a choice of a bell mode and a diaphragm mode; decomposing the bell mode or the diaphragm mode electrical signal into two component frequency ranges consisting of both a substantially lower frequency range and a substantially higher frequency range; and separately displaying the substantially lower frequency range and the substantially higher frequency range of the decomposed bell or diaphragm mode.

2. The method of claim 1 wherein the selectively filtered electrical heart signals corresponds to a choice of at least one of a low frequency murmur, a medium frequency murmur and a high frequency murmur.

3. The method of claim 1 wherein the heart sounds include at least an S1 heart sound and an S2 heart sound, and wherein the method further comprising ascertaining an onset of at least one of the heart sounds.

4. The method of claim 1 further comprising recording audio annotations associated with the patient.

5. The method of claim 1 further comprising displaying a composite heart signal from the selectively filtered electrical heart signals.

6. The method of claim 1 wherein the displayed heart signals are bracketed by a pair of calipers.

7. The method of claim 6 wherein the pair of calipers correspond to a time domain.

8. The method of claim 7 further comprising zooming on the displayed heart signals with respect to the time domain.

9. The method of claim 6 wherein the pair of calipers correspond to a frequency domain.

10. The method of claim 9 further comprising zooming on the displayed heart signals with respect to the frequency domain.

11. The method of claim 6 wherein the audio annotations are transcribed using speech recognition, and wherein the textual transcriptions of the audio annotations are recorded.

12. An auscultation system useful in association with a patient, the system comprising:
a sensor configured to sense heart sounds from at least one chest location of the patient and to transduce the heart sounds into electrical signals;
a signal processor configured to selectively filter the electrical signals thereby highlighting frequency differences of the heart sounds, and wherein the selectively filtered electrical heart signals corresponds to a choice of a bell mode and a diaphragm mode; the signal processor further configured to decompose the bell mode or the diaphragm mode electrical heart signal into two component frequency ranges consisting of both a substantially lower frequency range and a substantially higher frequency range; and a display configured to selectively display separately the substantially lower frequency range and the substantially higher frequency range of the selectively filtered electrical heart signal.

13. The auscultation system of claim 12 wherein the selectively filtered electrical heart signals corresponds to a choice of at least one of a low frequency murmur, a medium frequency murmur and a high frequency murmur.

14. The auscultation system of claim 12 wherein the heart sounds include at least an S1 heart sound and an S2 heart sound, and wherein the signal processor is further configured to ascertain an onset of at least one of the heart sounds.

15. The auscultation system of claim 12 further comprising memory for recording audio annotations associated with the patient.

16. The auscultation system of claim 12 wherein the displayed heart signals are bracketed by a pair of calipers.

17. The auscultation system of claim 16 wherein the pair of calipers correspond to a time domain.

18. The auscultation system of claim 17 wherein the display is further configured to zoom on the displayed heart signals with respect to the time domain.

19. The auscultation system of claim 16 wherein the pair of calipers correspond to a frequency domain.

20. The auscultation system of claim 19 wherein the display is further configured to zooming with respect to the frequency domain.

21. The auscultation system of claim 16 wherein the audio annotations are transcribed using speech recognition, and wherein the textual transcriptions of the audio annotations are recorded.

* * * * *